United States Patent [19]

Burgmaier et al.

[11] Patent Number: 4,810,626
[45] Date of Patent: Mar. 7, 1989

[54] SILVER HALIDE PHOTOSENSITIVE MATERIALS CONTAINING THIOUREA AND ANALOGUE COMPOUNDS

[75] Inventors: George J. Burgmaier, Pittsford; Arthur H. Herz, Rochester, both of N.Y.

[73] Assignee: Eastman Kodak Company, Rochester, N.Y.

[21] Appl. No.: 174,576

[22] Filed: Mar. 29, 1988

Related U.S. Application Data

[63] Continuation-in-part of Ser. No. 18,388, Feb. 25, 1987, abandoned.

[51] Int. Cl.[4] ................................................. G03C 1/10
[52] U.S. Cl. ..................................... 430/569; 430/600; 430/603
[58] Field of Search ................ 430/569, 600, 603, 611

[56] References Cited

U.S. PATENT DOCUMENTS

| | | | |
|---|---|---|---|
| 1,623,499 | 4/1927 | Sheppard et al. | 430/599 |
| 3,598,598 | 8/1971 | Herz | 430/611 |
| 4,221,863 | 9/1980 | Overman et al. | 430/567 |
| 4,284,712 | 8/1981 | Toya et al. | 430/603 |
| 4,469,783 | 9/1984 | Kuwabara et al. | 430/603 |
| 4,749,656 | 6/1988 | Herz et al. | 430/611 |

FOREIGN PATENT DOCUMENTS

0082408 7/1978 Japan .

Primary Examiner—Richard L. Schilling
Attorney, Agent, or Firm—Thomas F. Kirchoff

[57] ABSTRACT

A photographic silver halide emulsion comprising a 1,1,3,3-tetrasubstituted middle chalcogen urea compound is described wherein at least one substituent comprises a nucleophilic center. The urea compound is an effective chemical sensitizing agent. A process for chemically sensitizing silver halide is also described.

23 Claims, No Drawings

SILVER HALIDE PHOTOSENSITIVE MATERIALS CONTAINING THIOUREA AND ANALOGUE COMPOUNDS

This is a continuation-in-part of application Ser. No. 18,388, filed Feb. 25, 1987, now abandoned.

This invention relates to a silver halide photographic material and to a process for preparation thereof. In particular, this invention relates to use of a urea compound as a chemical sensitizing agent for silver halide.

Numerous thiourea compounds have been described as having utility in the photographic art. These uses include sensitization of silver halide. For example, U.S. Pat. No. 1,623,499 (1920) describes thiourea as a useful chemical sensitizing agent for silver halide.

U.S. Pat. No. 4,221,863 discloses the use of substituted thiourea compounds as agents for promoting the growth of silver halide grains during the precipitation and ripening steps. The identified thiourea compounds, typical of which is 1,1,3,3-tetramethyl-2-thiourea, are described as being capable of promoting uniform growth of silver halide grains with respect to both size and crystal habit. However, this patent does not relate to chemical sensitization of silver halide. Neither does it disclose the type of thiourea compounds which the instant applicants have found to be useful as chemical sensitizing agents for silver halide.

Japanese Public Disclosure 82408/1978 relates to the use of tetrasubstituted thiourea compounds as solvents for silver halide precipitation. The specifically illustrated compounds fail to describe a single tetrasubstituted thiourea compound having the substituents which are necessary to achieve chemical sensitization of silver halide. This is illustrated below by comparative data.

U.S. Pat. No. 4,284,717 describes tetrasubstituted thiourea compounds which are silver halide solvents. Included among these compounds are those having tertiary amine substituents on a urea nitrogen atom. However, as is shown below by comparative data, compounds comprising tertiary amine groups are not capable of imparting chemical sensitization to silver halide.

U.S. Pat. No. 3,598,598 describes tetra substituted thiourea compounds as useful fog-stabilizing agents. Among the described thiourea compounds are those containing carboxysubstituted phenyl groups. This patent contains no disclosure with respect to use of the described compounds as chemical sensitizing agents for silver halide and, as is demonstrated below by comparative data, a carboxyphenyl substituted thiourea compound such as described in the '598 patent is incapable of sensitizing silver halide.

Accordingly, there remains a need to obtain effective, yet inexpensive, chemical sensitizing agents for photographic silver halide emulsions.

The present invention provides a silver halide photographic material which comprises a sensitizing amount of a tetrasubstituted urea compound having the structural formula:

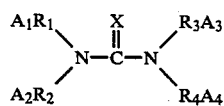

wherein

X is a middle chalcogen atom, i.e., a Group VI A atom below oxygen and above polonium;

each of $R_1$, $R_2$, $R_3$ and $R_4$ independently can represent an alkylene, cycloalkylene, carbocyclic arylene, heterocyclic arylene, alkarylene or aralkylene group; or taken together with the nitrogen atom to which they are attached, $R_1$ and $R_2$ or $R_3$ and $R_4$ can complete a 5 to 7 member heterocyclic ring; and each of $A_1$, $A_2$, $A_3$ and $A_4$ independently is hydrogen or represents a carboxylic, sulfinic, sulfonic, hydroxamic, mercapto, sulfonamido or primary or secondary amino nucleophilic group;

with the proviso that at least one of $A_1R_1$ to $A_4R_4$ contains the nucleophilic group bonded to a urea nitrogen atom through a 2 or 3 member chain.

Sulfur is the preferred Group VIA atom due to ready availability of starting materials for thiourea synthesis and greater solubility of the thiourea compound in aqueous solutions where silver halide sensitization occurs.

The term "nucleophilic" group, as employed in this invention, refers to an atom such as an oxygen atom of oxygen acids, a sulfur atom of sulfur acids and a nitrogen atom of nitrogen acids or of a primary or secondary amine. Such nucleophilic groups comprise carboxylic (—COOH), sulfinic (—$SO_2H$), sulfonic (—$SO_3H$), hydroxamic (—NHOH), mercaptan (—SH), sulfonamido (—$SO_2NH$—) and primary and secondary amines.

Inorganic or organic salts of these acids are equally useful.

Preferably, at least one of $R_1A_1$ to $R_4A_4$ is an omega-bound methyl or ethyl carboxylic acid or a salt thereof.

Other than a nucleophilic group as defined above, which is necessary for successful chemical sensitization of silver halide and which is attached to the urea nitrogen through a two or three member chain, the composition of the remaining RA groups on the 1,1,3,3-tetrasubstituted urea compound can vary widely for achieving the desired chemical sensitization of silver halides. This is shown below by comparative data.

Alkylene groups which can be represented by at least one of $R_1$ to $R_4$ which are not bonded to the required nucleophilic group can contain from 1 to 6 carbon atoms, preferably from 1 to about 4 carbon atoms for greater solubility properties.

When the $R_1$ to $R_4$ groups are cycloalkylene the ring portion can contain from about 3 to about 8, preferably about 5 or 6 carbon atoms. Where a cycloalkylene group has the required nucleophilic group bonded thereto it is important for successful operation of this invention that such group be bonded to one of the urea nitrogen atoms through a 2 or 3 member chain.

Where one of the $R_1$ to $R_4$ groups is an aromatic heterocyclic or an aromatic carbocyclic ring, such ring system can comprise from about 5 to about 10 atoms in the ring, such as for example pyrrole, phenyl, naphthyl, pyridinyl, quinolyl and naphthryl. When the aromatic heterocyclic or aromatic carbocyclic group has bonded thereto the required nucleophilic group, the chain separating the nucleophilic group from a urea nitrogen atom comprises from 2 to 3 members.

Where an $R_1$ to $R_4$ group is an alkarylene or aralkylene, the alkylene moiety thereof can comprise from about 1 to about 3 carbon atoms and the aryl portion is an aromatic group as described above. When the required nucleophilic group is bonded to an aralkylene group, the chain separating the nucleophilic group from a urea nitrogen atom comprises from 2 to 3 atoms.

Heterocyclic rings which can be formed by a urea nitrogen atom with $R_1$ and $R_2$ or with $R_3$ and $R_4$ can comprise 5 or 6 ring members. Typical heterocyclic rings so formed include pyridine, morpholine, piperdine and diazine.

Specific 1,1,3,3-tetrasubstituted-2-thiourea compounds useful in this invention include the following:

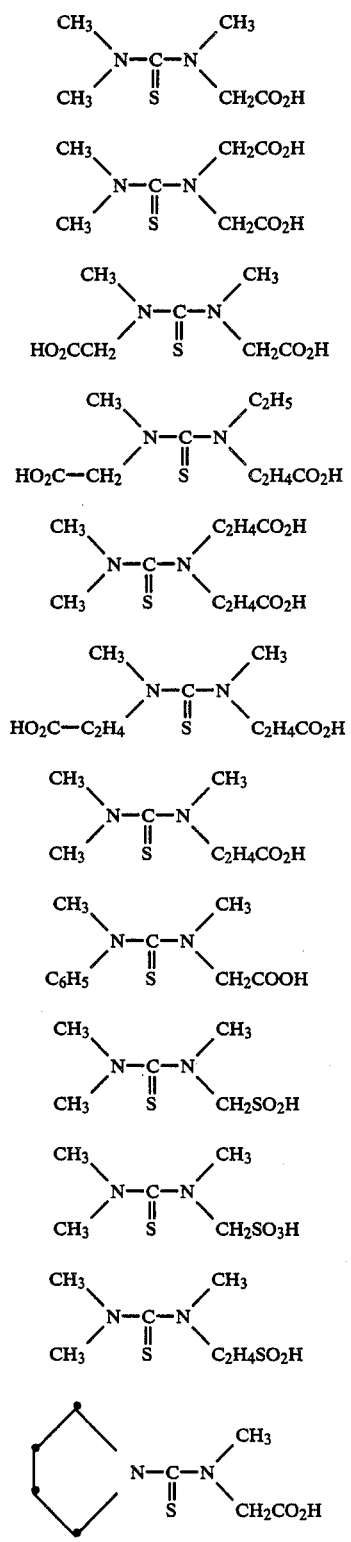

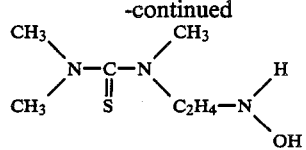

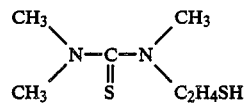

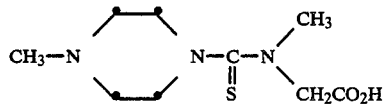

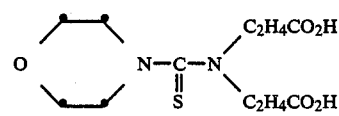

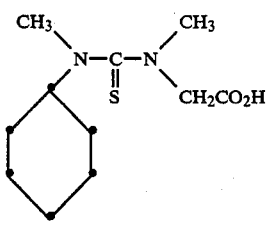

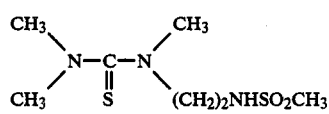

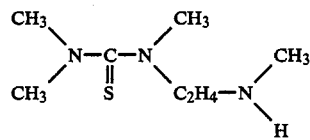

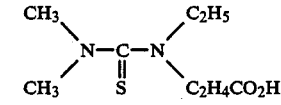

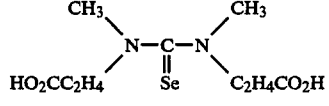

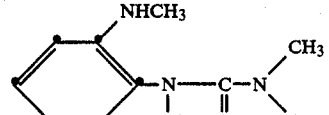

Synthesis of thiourea compounds of this invention can be effected by different techniques known in the art. One method, for example, comprises reacting an aliphatic monoaminocarboxylic acid with a dialkylthiocarbamoyl halide. This method is illustrated below with respect to preparation of Compound I.

Synthesis of Compound 1

(1-carboxymethyl-1,3,3-trimethyl-2-thiourea)

A. To a 500 ml flask was added 24.72 g (0.2 mol) dimethylthiocarbamoyl chloride, 30.72 g (0.2 mol) sarcosine ethyl ester hydrochloride, 300 ml dry acetonitrile and 80 ml (0.44 mol) diisopropylethylamine. The solution was heated with stirring at 55°-65° C. for 6.5 hours, cooled to room temperature, and concentrated to dryness. To the residue was added 200 ml ether, 200 ml water and 20 ml 12N HCl. The layers were separated and the aqueous phase extracted twice more with ether. The combined ether solutions were washed with 100 ml of 1N HCl and then with water. After drying over anhydrous magnesium sulphate, the solvent was removed, followed by distillation of the product, bp 130° C. at 0.15 mm Hg. The yield was 27.38 g (67%). The NMR, IR, and combustion analyses were consistent with the assigned structure for 1-ethoxycarbonylmethyl-1,3,3-trimethyl-2-thiourea.

B. To a solution of 75 ml water and 150 ml acetone was added 6 g (0.15 mol) of sodium hydroxide and 10.22 g (0.05 mol) of the above described 1-ethoxycarbonyl-methyl-1,3,3-trimethyl-2-thiourea. The solution was stirred at room temperature for 2.5 hours. After cooling in an ice bath, 13 ml of 12N HCl in 15 ml water was added. The solvent was removed at 50° C. under water aspirator pressure. 50 ml of isopropyl alcohol were added to the residue. The suspension was heated to reflux followed by decanting of the clear liquid. This step was repeated twice more with isopropyl alcohol. The isopropyl alcohol solutions were combined and concentrated in vacuo, leaving an oil. The combustion analyses, NMR, and IR were consistent with the assigned structure for Compound 1.

Selenourea Compound 21 was prepared from the diester of Compound 6, which was prepared as described above, and then converting the thiourea to the corresponding selenourea using a method similar to that described by D. L. Klayman and R. J. Shine, J. Chem. Soc. Chem. Commun, 1968, page 362, which publication is incorporated herein by reference.

This invention also provides a process for sensitizing a silver halide emulsion which is formed according to processes generally well known in the art. A double jet type process is preferred. The silver halide grains can comprise mixed or single halide components and especially include chloride, bromide, iodide, iodochloride, iodobromide or chlorobromide grains.

The double jet process comprises adding an aqueous silver nitrate solution and an aqueous solution of one or more halides, for example an alkali metal halide such as potassium bromide, potassium chloride, potassium iodide or mixtures thereof, simultaneously to a stirred solution of a silver halide protective colloid through two separate jets.

In the present invention the described sensitizing urea compounds may be added to a silver halide emulsion at various stages during its preparation. For example, the compounds may be added at levels from about $10^{-6}$ to about $10^{-2}$ mol thereof per mol of silver halide. A preferred concentration of urea compound to achieve sensitization of silver halide is from about $10^{-5}$ to about $10^{-3}$ mol thereof per mol of silver halide.

The urea sensitizing compounds may be added singly or in combination with other urea compounds, including other sensitizing agents. They may also be added to a silver halide emulsion along with silver ion ligands and silver halide growth modifiers or stabilizers and antifogging agents, or with spectral or chemical sensitizing agents, such as salts or complexes comprising iridium or gold, during formation of silver halide grains, during the physical or chemical ripening stage, or in a separate step before coating.

Conditions for sensitizing silver halide grains such as pH, pAg, temperature, etc., are not particularly limited when employed using compounds described herein. The pH is generally about 1 to 9, preferably about 2 to 6, and pAg is generally about 5 to about 12, preferably from about 7 to about 10. Silver halide grains may be sensitized at temperatures between about 30° to about 90° C., with about 35° C. to about 70° C. being preferred.

Gelatin is preferred as the binder or protective colloid for the photographic emulsion of the present invention. However, other hydrophilic colloids are also suitable. For example, proteins such as gelatin derivatives, graft polymers of gelatin and other polymers, albumin, casein, cellulose derivatives such as hydroxyethyl cellulose, carboxymethyl cellulose, cellulose sulfate, sugar derivatives such as sodium alginate, starch derivatives and various synthetic peptizers such as hydrophilic homopolymers or copolymers such as polyvinyl alcohol, poly-N-vinylpyrrolidone, polyacrylic acid, polymethacrylic acid, polyacrylamide, polyvinylimidazole, polyvinyl pyrazole can be used.

Acid-processed gelatin can be used as well as lime-processed gelatin. Further, gelatin hydrolyzates, and enzyme-hydrolyzed products of gelatin are also usable.

Surface active agents may be incorporated in a photographic emulsion layer or in another hydrophilic colloid layer as a coating aid to prevent build-up of static charge, to improve lubrication properties, to improve emulsion dispersion, to prevent adhesion, and to improve such photographic characteristics as acceleration of development, increase in contrast, or sensitization.

A photosensitive material of the present invention may contain antifogging agents or emulsion stabilizing agents, such as for example azaindenes, thionamides, azoles and the like.

The photosensitive material of the present invention may be spectrally sensitized with dyes. Dyes which can be used include cyanine dyes, merocyanine dyes, composite cyanine dyes, composite merocyanine dyes, and hemioxanol dyes. Particularly useful dyes are those belonging to the merocyanine class. These dyes contain as a basic heterocyclic ring nucleus any nucleus ordinarily used in cyanine dyes.

The photosensitive material of the present invention may contain color image-forming couplers, i.e., compounds capable of reacting with an oxidation product of an aromatic amine (usually a primary amine) to form a dye. Non-diffusing couplers containing a ballast group are desirable. Either 4-equivalent and 2-equivalent couplers are usable. In addition, colored couplers showing the effect of color correction, or couplers releasing a development inhibitor upon development (so-called DIR couplers) may be used.

A photosensitive material of the present invention is coated on a support conventionally used for photographic light-sensitive materials such as a flexible support (e.g., plastic film, paper, etc.) or a rigid support (e.g., glass, etc.) according to a dip-coating method, roller coating method, curtain coating method or extrusion coating method.

Emulsions used in the present invention can be applied to a multilayer multicolor photographic material comprising a support having provided thereon at least two layers having different spectral sensitivities. Multilayer multicolor photographic materials usually comprise a support having provided thereon at least one red-sensitive emulsion layer, at least one green-sensitive emulsion layer, and at least one blue-sensitive emulsion layer. The order of these layers can optionally be selected as occasion demands. Usually, a cyan-forming coupler is associated with the red-sensitive emulsion layer, a magenta-forming coupler is associated with the green-sensitive emulsion layer, and a yellow-forming coupler is associated with the blue-sensitive emulsion layer. In some cases, however, different layer arrangements may be employed.

The photosensitive materials obtained by the present invention can be processed according to known methods. A developer to be used for the black-and-white processing can contain conventional developing agents such as dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolidines or ascorbic acids.

As color-developing agent, there can be used primary aromatic amine developing agents such as phenylenediamines (e.g., 4-amino-N,N-diethylaniline, 3-methyl-4-amino-N,N-diethylaniline, 4-amino-N-ethyl-N-hydroxy-ethylaniline, 3-methyl-4-amino-N-ethyl-N-hydroxyethylaniline, 3-methyl-4-amino-N-ethyl-N-methanesulfonamidoethylaniline and 4-amino-3-methyl-N-ethyl-N-methoxyethylaniline. In addition, the developing agents described in L. F. A. Mason, Photographic Processing Chemistry (Focal Press, 1966), pp. 226–229, as well as those described in U.S. Pat. Nos. 2,193,015 and 2,592,364 may be used.

A photographic emulsion useful in the present invention can be applied to many different silver halide photographic light-sensitive materials due to its high photographic sensitivity, contrast, and fog reduction. For example, it can be used in high speed black-and-white negative films, in X-ray films and in multilayer color negative films.

The following examples further illustrate the invention. All parts, percents and ratios are by weight unless otherwise specified.

EXAMPLE 1

0.80 μm octahedral AgBr emulsions (pH 6.3, pBr 3.0), each containing 0.01 mmol/mol Ag of a thiourea compound indicated below, were heated for 30 minutes at 80° C., cooled and coated on a film support at 5813 mg Ag/m$^2$ and 10.018 mg gel/m$^2$. The coatings were dried and exposed (0.1 sec., 500 w 3000° K.) through a graduated density step wedge, processed (5 min. 20° C.) in Eastman Kodak Developer DK-50, washed and dried. The fog in each emulsion was less than 0.08 density unit. The relative speeds of compounds of the invention and of structurally similar compounds known in the art are shown below in Table I.

TABLE I $$\begin{array}{c} A_1-R^1 \diagdown \quad \diagup R^3A^3 \\ N-C-N \\ A_2-R^2 \diagup \underset{S}{\|} \diagdown R^4A^4 \end{array}$$

| Thiourea Compound | $A^1$ | $R^1$ | $A^2$ | $R^2$ | $A^3$ | $R^3$ | $A^4$ | $R^4$ | Relative Speed |
|---|---|---|---|---|---|---|---|---|---|
| None (control) | — | — | — | — | — | — | — | — | 100 |
| A (comparison) | H | H | H | H | H | H | H | H | 120 |
| B (comparison) | H | $CH_2$ | H | $CH_2$ | H | $CH_2$ | H | $CH_2$ | 97 |
| C (comparison) | H | $CH_2$ | p-$CO_2$H | $C_6H_4$ | H | $CH_2$ | p-$CO_2$H | $C_6H_4$ | 95 |
| D (comparison) | $CO_2$H | $C_3H_6$ | H | $CH_2$ | H | $CH_2$ | H | $CH_2$ | 102 |
| E (comparison) | $CO_2$H | $C_3H_6$ | H | $CH_2$ | H | $CH_2$ | $CO_2$H | $C_3H_6$ | 95 |
| 1 (invention) | $CO_2$H | $CH_2$ | H | $CH_2$ | H | $CH_2$ | H | $CH_2$ | 316 |
| 3 (invention) | $CO_2$H | $CH_2$ | H | $CH_2$ | H | $CH_2$ | $CO_2$H | $CH_2$ | 316 |
| 6 (invention) | $CO_2$H | $C_2H_4$ | H | $CH_2$ | H | $CH_2$ | $CO_2$H | $C_2H_4$ | 417 |

From the above results it is apparent that carboxymethyl (Compounds 1 and 3) and carboxyethyl (Compound 6) groups appreciably enhance the chemical sensitivity of otherwise ineffective thiourea and tetramethylthiourea compounds (A and B, respectively). The critical size of the divalent alkylene groups (R) of the compounds useful in this invention in comparison with other similar compounds is apparent by comparison of results from Compounds 6 and E. The addition of a single methylene (—$CH_2$—) group to the alkylene chains of Compound 6 drastically alters the chemical sensitization properties. Carboxyphenyl substitution on the thiourea structure fails to sensitize silver halide as is shown by Compound C results.

EXAMPLE 2

The same emulsions and conditions were used as in Example 1 except that instead of the 30 minute heat treatment at 80° C., the emulsions were kept for 120 minutes at 40° C. before coating. The compounds employed are identified in Table I.

TABLE II

| Thiourea Compound | Relative Speed |
|---|---|
| None (Control) | 100 |
| A | 138 |
| 6 | 661 |

Table II results make it apparent that compared to conventional chemical sensitizers like thiourea, a substituted thiourea of this invention is more effective for improving emulsion speed under relatively mild conditions.

EXAMPLE 3

8 mM cubic AgBr was dispersed at pH 3, pBr 3 in 0.02% ossein gelatin containing 28 mM $KNO_3$ and 0.6 mM of a thiourea compound. Following 17 hours agitation at 25° C., electronmicrographs were obtained and AgBr particle dimensions were evaluated with a Zeiss Particle Size Analyzer, MOP III. Results are reported in Table III. The compounds employed are identified above in Table 1.

TABLE III

| Compound | Equivalent Circular Diameter, in microns | Standard Deviation, microns |
|---|---|---|
| None (Control) | 0.166 | 0.004 |
| B | 0.203 | 0.005 |
| 3. | 0.164 | 0.003 |
| 6. | 0.168 | 0.004 |

The results show that whereas tetramethyl thiourea (Compound B), a known Ostwald ripener, increases AgBr particle size, the thiourea compounds disclosed herein had no detectable influence on crystal dimensions.

EXAMPLE 4

An octadehedral AgBr emulsion containing on average 0.5 micrometer crystals and with 40 g ossein gelatin/mol Ag, was given a sensitization treatment as noted below for 40 minutes at 70° C. The emulsions were coated at 2153 mg Ag and 3229 mg gelatin per m². The dried coatings were then exposed sensitometrically at 365 nm for 0.1 second and processed for 6 minutes in KODAK Rapid X-Ray Developer. Fog densities did not exceed 0.06. The tabulated speed values were normalized with respect to the control.

| Thiourea Sensitizing Agent (mg/Ag mol) | Relative Speed |
|---|---|
| Control (None) | 100 |
| Compound 3 (2 mg) | 372 |
| Compound 3 (2 mg), $KAuCl_4$ (4 mg) | 1510 |

These results make it apparent not only that a thiourea compound as described herein is by itself an effective sensitizer, but that it provides enhanced speed in combination with an ionic gold, chemical sensitizer.

EXAMPLE 5

Silver chloride emulsions containing cubic crystals of 0.29 micrometer edge length were given a sensitization treatment for 0.5 hours at 55° C. After cooling to 40° C. the emulsions were coated at 3229 mg Ag and 7535 mg gelatin per m². The dried coatings were exposed sensitometrically for 0.1 second and processed for 12 minutes in KODAK developer DK50. Fog densities did not exceed 0.1. The determined relative speeds shown below were normalized with respect to the control which contained no added sensitizing agent.

| Thiourea Sensitizer 0.46 mg/mol Ag | Relative Speed |
|---|---|
| Control (No sensitizer) | 100 |
| Compound 3 | 562 |

It is clear from these results that a thiourea of this invention can act as a highly effective AgCl sensitizer.

EXAMPLE 6

Silver bromoiodide emulsions (1.6 mol % iodide) having mean crystal diameters of 1.07 micrometers were treated near pBr3 and pH 6 for 9 minutes at 65° C. with sensitizing agent. After cooling to 40° C., the emulsions were coated at 334 mg Ag and 426 mg ossein gelatin per m². Following a 1/16 second sensitometric exposure and processing in Kodak DEKTOL DEVELOPER, speeds were determined. Results are shown below.

| Sensitizing Agent (mg/mol Ag) | Speed Relative to the Unsensitized Control |
|---|---|
| Control | 100 |
| Comparison F (2.02) | 110 |
| Compound 1 (0.32 mg) | 851 |
| Compound 21 (0.26 mg) | 661 |
| Compound 22 (1.62 mg) | 550 |

Comparison F is

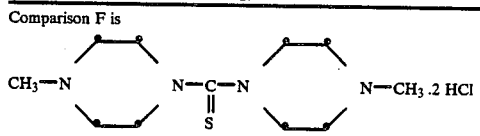

which is Compound 4 of U.S. Pat. No. 4,284,717.

As can be seen from the above results the tertiary amine compound, Comparison F, is far inferior to the urea compounds of this invention with respect to silver halide sensitizing ability.

This invention has been described in detail with particular reference to preferred embodiments thereof, but it will be understood that variations and modifications can be effected within the spirit and scope of the invention.

What is claimed is:

1. A silver halide photosensitive material comprising a sensitizing amount of a tetra-substituted urea compound having the structural formula:

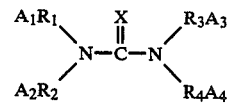

wherein

X is a middle chalcogen atom;

each of $R_1$, $R_2$, $R_3$ and $R_4$ independently can represent an alkylene, cycloalkylene, carbocyclic arylene or heterocyclic arylene, alkarylene or aralkylene group; or taken together with the nitrogen atom to which they are attached, $R_1$ and $R_2$ or $R_3$ and $R_4$ can complete a 5 to 7 member heterocyclic ring; and each of $A_1$, $A_2$, $A_3$ and $A_4$ independently is hydrogen or represents a carboxylic, sulfinic, sulfonic, hydroxamic, mercapto, sulfonamido or primary or secondary amino nucleophilic group;

with the proviso that at least one of $A_1R_1$ to $A_4R_4$ contains a nucleophilic group bonded to a urea nitrogen atom through a 2 or 3 member chain.

2. The photosensitive material of claim 1 wherein X is sulfur.

3. The photosensitive material of claim 2 wherein the nucleophilic group is a carboxylic, sulfinic, sulfonic or hydroxamic group.

4. The photosensitive material of claim 1 wherein the nucleophilic group is a carboxylic group.

5. The photosensitive material of claim 1 wherein the nucleophilic group is a primary or a secondary amino group.

6. The photosensitive material of claim 1 wherein the urea compound is present in an amount of from about $10^{-6}$ to about $10^{-2}$ mol thereof per mol of silver halide.

7. The photosensitive material of claim 6 wherein the urea compound is present in an amount of from about $10^{-5}$ to aboout $10^{-3}$ mol thereof per mol of silver halide.

8. The photosensitive material of claim 1 wherein the compound is:

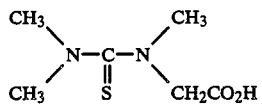

9. The photosensitive material of claim 1 wherein the compound is:

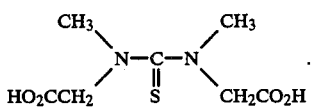

10. The photosensitive material of claim 1 wherein the compound is:

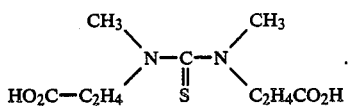

11. The photosensitive material of claim 1 wherein the compound is:

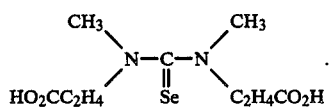

12. The photosensitive material of claim 1 wherein the compound is:

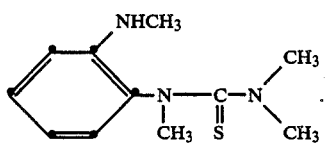

13. In a process for the sensitization of a silver halide emulsion, the improvement which comprises adding, during preparation of said emulsion, from about $10^{-6}$ to about $10^{-2}$ mol per mol of silver halide of a compound having the structural formula:

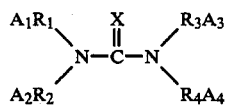

wherein
X is a middle chalcogen atom;
each of $R_1$, $R_2$, $R_3$ and $R_4$ independently can represent an alkylene, cycloalkylene, carbocyclic arylene, heterocyclic arylene, alkarylene or aralkylene group, or taken together with the nitrogen atom to which they are attached, $R_1$ and $R_2$ or $R_3$ and $R_4$ can complete a 5 to 7 member heterocyclic ring; and
each of $A_1$, $A_2$, $A_3$ and $A_4$ independently is hydrogen or represents a carboxylic, sulfinic, sulfonic, hydroaminic, mercapto, sulfonamido or primary or secondary amino nucleophilic group;
with the proviso that at least one of $A_1R_1$ to $A_4R_4$ contains a nucleophilic group bonded to a urea nitrogen atom through a 2 or 3 member chain.

14. The process of claim 13 wherein X is sulfur.

15. The process of claim 14 wherein the nucleophilic group is a carboxylic, sulfinic, sulfonic or hydroxamic group.

16. The process of claim 13 wherein the nucleophilic group is a carboxylic group.

17. The process of claim 13 wherein the nucleophilic group is a primary or a secondary amino group.

18. The process of claim 13 wherein the compound is present in an amount of from about $10^{-5}$ to about $10^{-3}$ mol thereof per mol of silver halide.

19. The process of claim 13 wherein the compound has the structural formula:

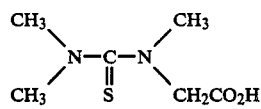

20. The process of claim 13 wherein the compound has the structural formula:

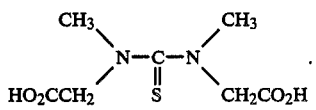

21. The process of claim 13 wherein the compound has the structural formula:

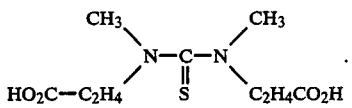

22. The process of claim 13 wherein the compound has the structural formula:

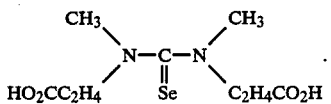

23. The process of claim 13 wherein the compound has the structural formula:

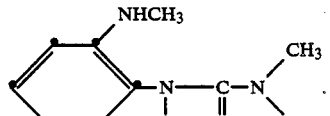

* * * * *